United States Patent
Callens et al.

(10) Patent No.: US 10,294,013 B2
(45) Date of Patent: May 21, 2019

(54) PACKAGE TO DISPENSE A FOAMING COMPOSITION

(71) Applicant: The Procter & Gamble Company, Cincinnati, OH (US)

(72) Inventors: Cedric Kofi Aurelien Callens, Singapore (SG); Stefano Bartolucci, Singapore (SG); William Mercer Benson, Harrison, OH (US)

(73) Assignee: The Procter and Gamble Plaza, Cincinnati, OH (US)

( * ) Notice: Subject to any disclaimer, the term of this patent is extended or adjusted under 35 U.S.C. 154(b) by 0 days.

(21) Appl. No.: 15/381,298

(22) Filed: Dec. 16, 2016

(65) Prior Publication Data

US 2017/0174413 A1   Jun. 22, 2017

Related U.S. Application Data

(60) Provisional application No. 62/270,053, filed on Dec. 21, 2015.

(51) Int. Cl.
*B65D 83/62*   (2006.01)
*B65D 83/14*   (2006.01)
(Continued)

(52) U.S. Cl.
CPC .............. *B65D 83/62* (2013.01); *A61K 8/046* (2013.01); *A61K 8/342* (2013.01); *A61K 8/416* (2013.01);
(Continued)

(58) Field of Classification Search
CPC ................................ B65D 83/62; A61K 8/046
(Continued)

(56) References Cited

U.S. PATENT DOCUMENTS 3,236,733 A   2/1966   Karsten et al.
3,938,708 A * 2/1976   Burger ................... B65D 83/62
                                                        222/192
(Continued)

FOREIGN PATENT DOCUMENTS

DE   10304721 B4   3/2007
EP     978271 A1   2/2000
(Continued)

OTHER PUBLICATIONS

U.S. Appl. No. 15/380,194, filed Dec. 15, 2016, Glenn, Jr. et al.
(Continued)

*Primary Examiner* — Vishal Pancholi
(74) *Attorney, Agent, or Firm* — Angela K. Haughey

(57) ABSTRACT

Disclosed is a package to dispense a composition, wherein the package comprises:
a flexible inner container made of gas-impermeable material and holding the composition wherein the composition comprises a blooming agent in an emulsified liquid form;
a sealed rigid outer container which encloses the flexible inner container and which is filled with a driving gas compressing the inner container; and
a dispenser attached to the inner container and in a fluid connection with the composition by which the composition is allowed to be dispensed by the pressure of the driving gas;
wherein the pressure of the driving gas is higher than the vapor pressure of the emulsified liquid blooming agent in the inner container, throughout the usage of the package until the exhaustion of the composition in the inner container.

17 Claims, 1 Drawing Sheet

(51) Int. Cl.
  *A61K 8/34* (2006.01)
  *A61K 8/41* (2006.01)
  *A61K 8/04* (2006.01)
  *A61K 8/69* (2006.01)
  *A61K 8/92* (2006.01)
  *A61Q 5/12* (2006.01)

(52) U.S. Cl.
  CPC ............. *A61K 8/69* (2013.01); *A61K 8/922* (2013.01); *A61Q 5/12* (2013.01); *B65D 83/752* (2013.01); *A61K 2800/87* (2013.01)

(58) Field of Classification Search
  USPC .................. 222/62, 94, 386.5, 632, 635
  See application file for complete search history.

(56) References Cited

U.S. PATENT DOCUMENTS

| | | |
|---|---|---|
| 4,610,874 A | 9/1986 | Matravers |
| 4,880,618 A | 11/1989 | Grollier et al. |
| 5,077,040 A | 12/1991 | Bergmann et al. |
| 5,635,469 A | 6/1997 | Fowler et al. |
| 6,039,036 A | 3/2000 | Restle et al. |
| 6,589,509 B2 | 7/2003 | Keller et al. |
| 6,604,693 B2 | 8/2003 | Santagiuliana |
| 6,605,577 B1 | 8/2003 | Harrison et al. |
| 6,642,194 B2 | 11/2003 | Harrison et al. |
| 7,001,594 B1 | 2/2006 | Peffly et al. |
| 7,217,777 B2 | 5/2007 | Lange et al. |
| RE40,534 E | 10/2008 | Harrison et al. |
| 7,455,195 B2 | 11/2008 | Mekata |
| 7,470,651 B2 | 12/2008 | Uehara et al. |
| 7,504,093 B2 | 3/2009 | Bracken et al. |
| 8,017,106 B2 | 9/2011 | Keller et al. |
| 8,475,777 B2 | 7/2013 | Rautschek |
| 8,476,472 B2 | 7/2013 | Hojo et al. |
| 9,255,184 B2 | 2/2016 | Paul |
| 9,308,398 B2 | 4/2016 | Hutton et al. |
| 9,358,186 B2 | 6/2016 | Chandra et al. |
| 9,539,199 B2 | 1/2017 | Beer et al. |
| 9,539,208 B2 | 1/2017 | Tamarkin et al. |
| 9,540,489 B2 | 1/2017 | Panandiker et al. |
| 9,993,419 B2 | 6/2018 | Glenn, Jr. et al. |
| 9,993,420 B2 | 6/2018 | Glenn, Jr. et al. |
| 10,123,963 B2 | 11/2018 | Glenn, Jr. et al. |
| 10,124,951 B2 | 11/2018 | Glenn, Jr. et al. |
| 2001/0008630 A1 | 7/2001 | Pyles et al. |
| 2001/0025857 A1* | 10/2001 | Baudin ................ B65D 83/38 222/95 |
| 2002/0031532 A1 | 3/2002 | Uchiyama |
| 2002/0143063 A1 | 10/2002 | Alvarado |
| 2002/0197213 A1 | 12/2002 | Schmenger et al. |
| 2003/0228272 A1 | 12/2003 | Amjad et al. |
| 2004/0018164 A1 | 1/2004 | Zofchak et al. |
| 2004/0076595 A1 | 4/2004 | Khan |
| 2004/0229763 A1 | 11/2004 | Hutton, III et al. |
| 2004/0247550 A1 | 12/2004 | Asari et al. |
| 2005/0002892 A1 | 1/2005 | Khan et al. |
| 2005/0136011 A1 | 6/2005 | Nekludoff et al. |
| 2005/0196372 A1 | 9/2005 | Cajan |
| 2005/0196376 A1 | 9/2005 | Loomis |
| 2005/0197421 A1 | 9/2005 | Loomis |
| 2005/0222001 A1 | 10/2005 | Baumeister et al. |
| 2005/0274737 A1* | 12/2005 | Krause ................ B65D 83/62 222/105 |
| 2006/0034792 A1 | 2/2006 | Lazzeri et al. |
| 2006/0054634 A1* | 3/2006 | Mekata ............ B05B 11/0043 222/94 |
| 2006/0078583 A1 | 4/2006 | Rennie |
| 2006/0083704 A1 | 4/2006 | Torgerson |
| 2006/0275245 A1 | 12/2006 | Decoster et al. |
| 2006/0292104 A1 | 12/2006 | Guskey et al. |
| 2006/0293197 A1 | 12/2006 | Uehara et al. |
| 2007/0286837 A1 | 12/2007 | Torgerson |
| 2008/0066773 A1 | 3/2008 | Anderson et al. |
| 2008/0138296 A1 | 6/2008 | Tamarkin et al. |
| 2008/0292560 A1 | 11/2008 | Tamarkin et al. |
| 2008/0292574 A1 | 11/2008 | Uehara |
| 2009/0041706 A1 | 2/2009 | Molenda et al. |
| 2010/0143280 A1 | 6/2010 | Yokogi et al. |
| 2010/0143281 A1 | 6/2010 | Okada et al. |
| 2010/0143282 A1 | 6/2010 | Yokogi et al. |
| 2010/0143425 A1 | 6/2010 | Okada et al. |
| 2010/0178265 A1 | 7/2010 | Molenda et al. |
| 2011/0135588 A1 | 6/2011 | Uehara et al. |
| 2011/0226273 A1 | 9/2011 | Deardorff et al. |
| 2011/0280110 A1 | 11/2011 | Chen |
| 2011/0318295 A1 | 12/2011 | Shimizu |
| 2012/0020908 A1 | 1/2012 | Paul |
| 2012/0034173 A1 | 2/2012 | Batt et al. |
| 2012/0043352 A1* | 2/2012 | Rasmussen ........ B67D 1/0412 222/386.5 |
| 2012/0114819 A1 | 5/2012 | Ragnarsson |
| 2012/0171147 A1 | 7/2012 | Rautschek |
| 2012/0288465 A1 | 11/2012 | Loechel |
| 2013/0075430 A1 | 3/2013 | Ragnarsson |
| 2013/0202666 A1 | 8/2013 | Petkov et al. |
| 2013/0280192 A1 | 10/2013 | Carter et al. |
| 2013/0284196 A1 | 10/2013 | Murdock et al. |
| 2014/0105943 A1 | 4/2014 | Pistoria et al. |
| 2014/0107224 A1* | 4/2014 | Osman ................ A61K 9/0019 514/723 |
| 2014/0116458 A1 | 5/2014 | Krueger |
| 2014/0135414 A1 | 5/2014 | Loomis |
| 2014/0237732 A1 | 8/2014 | Zuedel Fernandes et al. |
| 2014/0302103 A1 | 10/2014 | Carter et al. |
| 2014/0356303 A1 | 12/2014 | Rocco et al. |
| 2014/0377206 A1 | 12/2014 | Uehara et al. |
| 2015/0011450 A1 | 1/2015 | Carter et al. |
| 2015/0030643 A1 | 1/2015 | Gartstein et al. |
| 2015/0093420 A1 | 4/2015 | Snyder et al. |
| 2015/0190326 A1 | 7/2015 | Brouard et al. |
| 2015/0359725 A1 | 12/2015 | Glenn, Jr. et al. |
| 2015/0359726 A1 | 12/2015 | Glenn, Jr. et al. |
| 2015/0359727 A1 | 12/2015 | Glenn, Jr. et al. |
| 2015/0359728 A1 | 12/2015 | Glenn, Jr. et al. |
| 2016/0000673 A1 | 1/2016 | Ainger et al. |
| 2016/0310375 A1 | 4/2016 | Torres Rivera et al. |
| 2016/0310376 A1 | 4/2016 | Torres Rivera et al. |
| 2016/0143821 A1 | 5/2016 | Chang et al. |
| 2016/0309871 A1 | 10/2016 | Torres Rivera et al. |
| 2016/0310371 A1 | 10/2016 | Zhao et al. |
| 2016/0310372 A1 | 10/2016 | Glenn, Jr. et al. |
| 2016/0310377 A1 | 10/2016 | Torres Rivera et al. |
| 2016/0310397 A1 | 10/2016 | Johnson et al. |
| 2017/0087068 A1 | 3/2017 | Callens et al. |
| 2017/0165164 A1 | 6/2017 | Zhao et al. |
| 2017/0165165 A1 | 6/2017 | Zhao et al. |
| 2018/0168948 A1 | 6/2018 | Glenn, Jr. et al. |
| 2018/0168949 A1 | 6/2018 | Glenn, Jr. et al. |
| 2018/0168996 A1 | 6/2018 | Glenn, Jr. et al. |
| 2018/0221270 A1 | 8/2018 | Glenn, Jr. et al. |
| 2018/0256457 A1 | 9/2018 | Glenn, Jr. et al. |
| 2018/0256459 A1 | 9/2018 | Torres Rivera et al. |
| 2018/0256481 A1 | 9/2018 | Glenn, Jr. et al. |
| 2018/0353398 A1 | 12/2018 | Torres Rivera et al. |

FOREIGN PATENT DOCUMENTS

| | | |
|---|---|---|
| EP | 1340485 A2 | 2/2003 |
| EP | 2138155 A2 | 12/2009 |
| JP | H06227941 A | 8/1994 |
| JP | 2001302466 A | 10/2001 |
| JP | 2003-119113 A | 4/2003 |
| JP | 2005232271 A | 9/2005 |
| JP | 2006182743 A | 7/2006 |
| JP | 2010-132569 A | 6/2010 |
| JP | 4694171 B2 | 6/2011 |
| JP | 2014-125477 A | 7/2014 |
| WO | WO 96/19188 A1 | 6/1996 |
| WO | WO 97/20626 A1 | 6/1997 |

(56) References Cited

FOREIGN PATENT DOCUMENTS

| WO | WO 2004/078901 A1 | 9/2004 |
|---|---|---|
| WO | WO2006045170 A2 | 5/2006 |
| WO | WO 2013/176666 A1 | 11/2013 |

OTHER PUBLICATIONS

U.S. Appl. No. 15/380,218, filed Dec. 15, 2016, Glenn, Jr. et al.
U.S. Appl. No. 15/380,261, filed Dec. 15, 2016, Glenn, Jr. et al.
U.S. Appl. No. 15/380,293, filed Dec. 15, 2016, Glenn, Jr. et al.
U.S. Appl. No. 15/380,345, filed Dec. 15, 2016, Glenn, Jr. et al.
U.S. Appl. No. 15/380,373, filed Dec. 15, 2016, Glenn, Jr. et al.
U.S. Appl. No. 15/492,429, filed Apr. 20, 2017, Glenn, Jr. et al.
U.S. Appl. No. 15/492,451, filed Apr. 20, 2017, Glenn, Jr. et al.
U.S. Appl. No. 15/492,469, filed Apr. 20, 2017, Glenn, Jr. et al.
U.S. Appl. No. 62/435,267, filed Dec. 16, 2016, Glenn, Jr. et al.
U.S. Appl. No. 62/435,271, filed Dec. 16, 2016, Glenn, Jr. et al.
U.S. Appl. No. 62/435,296, filed Dec. 16, 2016, Glenn, Jr. et al.
All Office Actions, U.S. Appl. No. 14/739,588, P&G Case 13425M.
All Office Actions, U.S. Appl. No. 14/739,670, P&G Case 13426M.
All Office Actions, U.S. Appl. No. 14/739,708, P&G Case 13427M.
All Office Actions, U.S. Appl. No. 14/739,755, P&G Case 13428M.
All Office Actions, U.S. Appl. No. 15/135,684, P&G Case 13812M.
All Office Actions, U.S. Appl. No. 15/135,691, P&G Case 13813M.
All Office Actions, U.S. Appl. No. 15/135,705, P&G Case 13814M.
All Office Actions, U.S. Appl. No. 15/135,715, P&G Case 13817M.
All Office Actions, U.S. Appl. No. 15/380,194, P&G Case 14168M.
All Office Actions, U.S. Appl. No. 15/380,218, P&G Case 14169M.
All Office Actions, U.S. Appl. No. 15/380,261, P&G Case 14170M.
All Office Actions, U.S. Appl. No. 15/380,293, P&G Case 14171M.
All Office Actions, U.S. Appl. No. 15/380,345, P&G Case 14172M.
All Office Actions, U.S. Appl. No. 15/380,373, P&G Case 14173M.
All Office Actions, U.S. Appl. No. 15/135,712, P&G Case 13804M.
All Office Actions, U.S. Appl. No. 15/274,226, P&G Case AA1034M.
All Office Actions, U.S. Appl. No. 15/136,020, P&G Case 13821M.
All Office Actions, U.S. Appl. No. 15/136,032, P&G Case 13822M.
All Office Actions, U.S. Appl. No. 15/492,429, P&G Case 14321M.
All Office Actions, U.S. Appl. No. 15/492,451, P&G Case 14322M.
All Office Actions, U.S. Appl. No. 15/492,469, P&G Case 14323M.
Carolyn Evans: "Scalp Cleansing, Scalp Tonique, Hair Shampoo, Hair Conditioner, Demonstration" Youtube, Apr. 22, 2012, p. 2. First part of the video (0-3 min) dedicated to "scalp cleansing"; second part of the video (3-6 min) dedicated to the treatment of the hair.
Anonymous: "GNPD—Anti-Dandruff Shampoo", Nov. 1, 2012.
Anonymous "Shampoo only Scalp? or entire head?—The Long Hair Community Discussion Boards", Feb. 1, 2011, Retrieved from the internet: URL: http://forums.longhaircommunity.com/archieve/index.php/t-91788.html, retrieved on Jul. 21, 2016.
Samantha Zabell: "Mistakes You're Making Washing Your Hair—How You're Washing Your Hair Wrong", Jan. 14, 2014, Retrieved from the Internet: URL: http://www.goodhousekeeping.com/beauty/hair/tips/a19894/mistakes-washing-your-hair/, Section 3. "Overdoing it on shampoo and/or conditioner"; p. 2, retrieved on Jul. 21, 2016.
Anonymous: "GNPD—Anti-Dandruff Shampoo + Conditioner Set", Procter and Gamble China, Apr. 1, 2009, Mintel GNPD, Retrieved from the Internet: URL: http://www.gnpd.com/sinatra/recordpage/107827/from_search/EkXVQ1u6vF/?p.=2, Retrieved on Jul. 12, 2016.
Database GNPD, Mintel; Aug. 2014 "Gold Olive Haircare Set".
Database GNPD Mintel; May 2014, "Coconut & Macadamia Oil Nourishing Shampoo and Nourishing Conditioner".
"Clarifying Shampoo", Mintel, Jun. 2015.
"Reinforcing conditioner", Mintel, May 2014.
Silsoft* 251, amine functional silicone microemulsion, Momentive Marketing Bulletin, 2012, 2 pages.
In-Cosmetics 2012: Wacker Introduced Novel Silicone Emulsions and New Hybrid Polymer for Hair-Care and Hair-Styling Products, Apr. 17, 2012, Munich.
PCT International Search Report and Written Opinion for PCT/US2016/066753 dated Feb. 28, 2017, 11 pages.
PCT International Search Report and Written Opinion for PCT/US2016/067916 dated Mar. 29, 2016.
PCT International Search Report and Written Opinion for PCT/US2016/028731 dated Jul. 5, 2016, 11 pages.
PCT International Search Report and Written Opinion for PCT/US2016/028860 dated Jul. 7, 2016, 11 pages.
PCT International Search Report and Written Opinion for PCT/US2015/035796 dated Sep. 14, 2015, 9 pages.
PCT International Search Report and Written Opinion for PCT/US2015/035756 dated Dec. 21, 2015, 13 pages.
PCT International Search Report and Written Opinion for PCT/US2015/035797 dated Sep. 14, 2015, 9 pages.
PCT International Search Report and Written Opinion for PCT/US2015/035799 dated Sep. 14, 2015, 9 pages.
PCT International Search Report and Written Opinion for PCT/US2016/028739 dated Jul. 4, 2016, 11 pages.
PCT International Search Report and Written Opinion for PCT/US2016/066755 dated Feb. 27, 2017, 12 pages.
PCT International Search Report and Written Opinion for PCT/US2016/066759 dated Feb. 27, 2017, 11 pages.
PCT International Search Report and Written Opinion for PCT/US2016/066754 dated Feb. 20, 2017, 11 pages.
PCT International Search Report and Written Opinion for PCT/US2016/028745 dated Aug. 8, 2016.
PCT International Search Report and Written Opinion for PCT/US2016/028853 dated Sep. 30, 2016, 19 pages.
PCT International Search Report and Written Opinion for PCT/US2016/028855, dated Oct. 5, 2016, 18 pages.
PCT International Search Report and Written Opinion for PCT/US2016/028743 dated Jul. 25, 2016.
U.S. Appl. No. 15/843,069, filed Dec. 15, 2017, Glenn, Jr. et al.
U.S. Appl. No. 15/843,146, filed Dec. 15, 2017, Glenn, Jr. et al.
U.S. Appl. No. 15/843,178, filed Dec. 15, 2017, Glenn, Jr. et al.
All final and non-final office action for U.S. Appl. No. 15/972,763 (P&G Case 13814MC).
All final and non-final office action for U.S. Appl. No. 15/973,845 (P&G Case 13425MC).
All final and non-final office action for U.S. Appl. No. 15/978,667 (P&G Case 13817MC).
PCT International Search Report and Written Opinion for PCT/US2017/066561 dated Apr. 4, 2018.
PCT International Search Report and Written Opinion for PCT/US2017/066563 dated Apr. 4, 2018.
U.S. Appl. No 15/946,275, filed Apr. 5, 2018, Glenn, Jr. et al.
U.S. Appl. No 15/972,763, filed May 7, 2018, Glenn, Jr. et al.
U.S. Appl. No 15/978,667, filed May 14, 2018, Glenn, Jr. et al.
U.S. Appl. No 15/973,845, filed May 8, 2018 Glenn, Jr. et al.
All final and non-final office actions for U.S. Appl. No. 16/104,343 (P&G Case 13812MC).

* cited by examiner

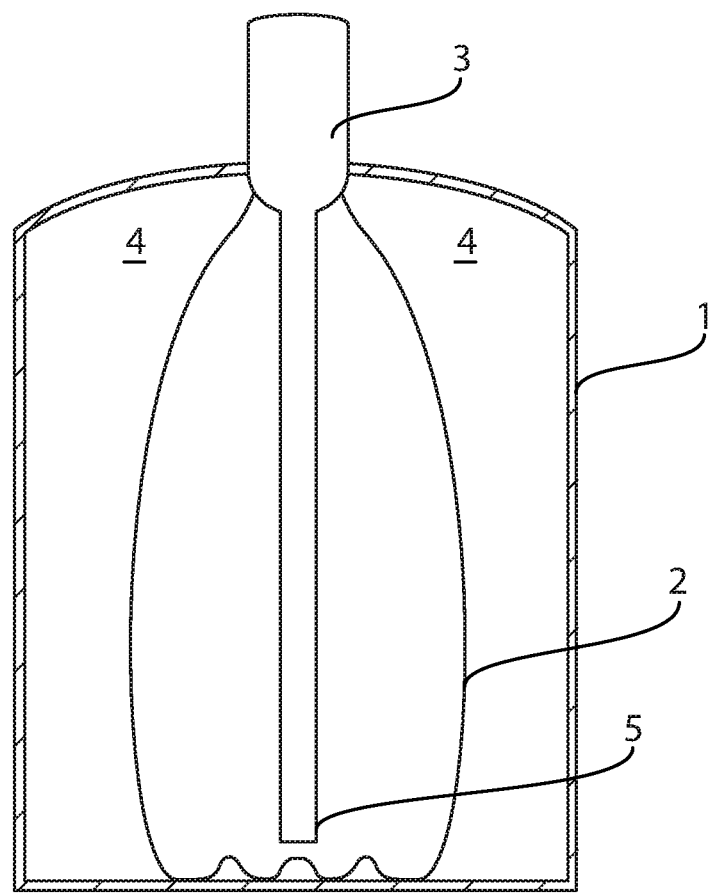

PACKAGE TO DISPENSE A FOAMING COMPOSITION

FIELD OF THE INVENTION

The present invention relates to a package to dispense a composition, wherein the package comprises: a flexible inner container made of gas-impermeable material and holding the composition wherein the composition comprises a blooming agent in an emulsified liquid form; a sealed rigid outer container which encloses the flexible inner container and which is filled with a driving gas compressing the inner container; and a dispenser attached to the inner container and in a fluid connection with the composition by which the composition is allowed to be dispensed by the pressure of the driving gas; wherein the pressure of the driving gas is higher than the vapor pressure of the emulsified liquid blooming agent in the inner container, throughout the usage of the package until the exhaustion of the composition in the inner container. This package prevents package failures (particularly inner container bursting), and/or provides reduced sputtering, reduced noise when dispensing, and/or reduced an amount of residues which are compositions remaining in the package.

BACKGROUND OF THE INVENTION

A wide variety of cosmetic compositions have been proposed in a variety of product forms such as liquid, oil, creams, gels, emulsions, foams/mousses and sprays.

As for foams/mousses, for example, EP2535037 (which is also published as WO2012/154918) discloses a cosmetic composition in a container comprising at least one inner bag and an outer container, wherein the outer container encloses the inner bag and is filled with a propellant compressing the inner bag; and a valve mechanism attached to the inner bag moveable between an open position, in which a composition stored in the inner bag is allowed to be discharged by the pressure of the compressed gas as a foam, and a closed position, in which the composition is not allowed to be discharged, wherein the composition within the inner bag comprises: a) 0.1 to 5% by weight of a cationic surfactant (A); b) 0.1 to 10% by weight of a fatty alcohol (B); and 0.1 to 10% by weight of carbon dioxide. EP2535037 discloses that the objective of the invention is to provide a container with at least one inner bag, e.g., a bag-on-valve-system, in an outer container, containing a stable foam, especially a rich, thick and creamy mousse. EP2535037 also discloses a composition in Example comprising 0.4% of cetrimonium chloride, 1.8% of cetearyl alcohol, and 2.0% of carbon dioxide. EP2535037 further discloses that the pressure of the propellant is preferably set to 0.3 to 1.0 MPa, preferably to about 0.8 MPa, from the perspective of stably discharging the content of the bag until the preferably complete exhaustion of the composition contained in the bag.

Another example can be US 2004/0166064 disclosing a packaged gas-solubilized product comprising: (a) a product having dissolved in it a first gas with a first pressure; and (b) an assembly for holding and dispensing the gas-solubilized product, the assembly comprising: a sealed rigid outer container; a flexible inner container made of gas-impermeable material and holding the gas-solubilized product, the inner container hermetically disposed inside the outer container, whereby a space is formed between the inner and the outer containers, wherein the space is charged with a second gas with an initial charging pressure, wherein the initial charging pressure is higher than the first pressure; and a product dispenser in a fluid connection with the product contained in the internal container. US 2004/0166064 also discloses in paragraph [0020] that the product containing the dissolved gas may be in a form selected from the group consisting of milk, cream, lotion, gel, paste, spray, and aerosol foam. US 2004/0166064 further discloses in paragraph [0050] that "the pressure of the second gas is not limited as long as the outside container 1 can withstand the pressure of the second gas after the inner container 2 is filled and as long as the charging pressure of the second gas is higher than the partial pressure of the dissolved first gas. In one embodiment, the first pressure is from about 15 to 250 psig, and the second pressure is from about 50 to about 300 psig. Other considerations that may affect pressure specifications are the product viscosity, desired dispensation force and container size, provided the pressure of the second gas remains higher than the partial pressure of the first gas."

However, it has been found by the inventors of the present invention that such foam dispensing systems may not be entirely satisfactory to consumers, especially in view of package failures (particularly inner container bursting), sputtering, noise when dispensing, and/or an amount of residues which are compositions remaining in the package. Thus, the inventors of the present invention have found a need to prevent package failures, and/or to improve sensory experience such as reduced sputtering, reduced noise when dispensing, and/or reduced amount of residues which are compositions remaining in the package. The inventors of the present invention have also found that such needs may be increased especially when the composition to be dispensed meets at least one of the following conditions:

having a higher foam density;

employing a higher vapor pressure of a blooming agent mixed with the composition to foam; and/or being dispensed as delayed foams and/or blooming foams (dispensing composition as creams then turning into foams).

SUMMARY OF THE INVENTION

The present invention is directed to a package to dispense a composition, wherein the package comprises:

a flexible inner container made of gas-impermeable material and holding the composition wherein the composition comprises a blooming agent in an emulsified liquid form;

a sealed rigid outer container which encloses the flexible inner container and which is filled with a driving gas compressing the inner container; and a dispenser attached to the inner container and in a fluid connection with the composition by which the composition is allowed to be dispensed by the pressure of the driving gas;

wherein the pressure of the driving gas is higher than the vapor pressure of the emulsified liquid blooming agent in the inner container, throughout the usage of the package until the exhaustion of the composition in the inner container.

This package of the present invention prevents package failures (particularly inner container bursting), and/or provides reduced sputtering, reduced noise when dispensing, and/or reduced an amount of residues which are compositions remaining in the package, even when the composition to be dispensed meets the following conditions:

having a higher foam density;

employing a higher vapor pressure of a blooming agent mixed with the composition to foam; and/or being dispensed as delayed foams and/or blooming foams (dispensing composition as creams then turning into foams).

The inventors of the present invention have surprisingly found that, in the existing foam dispensing systems, the compositions generally start to foam inside of the package i.e. before dispensing, and this is associated to package failures (particularly bag bursting), sputtering, noise when dispensing, and/or an increased amount of residues which are compositions remaining in the package, especially when the composition to be dispensed meets at least one of the following conditions:

having a higher foam density;

employing a higher vapor pressure of a blooming agent mixed with the composition to foam; and/or being dispensed as delayed foams and/or blooming foams (dispensing composition as creams then turning into foams).

The inventors of the present invention have solved these problems by controlling the pressure of the driving gas and the vapor pressure of the emulsified liquid blooming agent, such that the pressure of the driving gas is higher than the vapor pressure of the emulsified liquid blooming agent in the inner container, throughout the usage of the package until the exhaustion of the composition in the inner container.

The benefit of the present invention can be observed more clearly when non-emulsified blooming agent vapor pressure is 30 psig or above, and the composition is dispensed as delayed foams and/or blooming foams.

Such delayed foaming and/or gradual foaming is, for example, that it takes for at least about 10 seconds, preferably at least about 20 seconds, more preferably at least about 30 seconds for the composition to be completely foamed. In such delayed foaming and/or gradual foaming, the composition is dispensed from the package as creams, and then gradually turning into foams. Such delayed foaming and/or gradual foaming may provide easiness to control the application amount, and/or easiness to apply as it may spreads as creams then turning into foams. For example, when the composition is a hair care composition, this transformation during application may increase the contact with hair

DETAILED DESCRIPTION OF THE INVENTION

FIG. 1 shows a front view of a package to dispense a foaming composition.

DETAILED DESCRIPTION OF THE INVENTION

In all embodiments of the present invention, all percentages are by weight of the total composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

The term "comprising," as used herein, means that other steps and other ingredients which do not affect the end result can be added. This term encompasses the terms "consisting of" and "consisting essentially of." The compositions and methods/processes of the present invention can comprise, consist of, and consist essentially of the elements and limitations of the invention described herein, as well as any of the additional or optional ingredients, components, steps, or limitations described herein.

The terms "include," "includes," and "including," as used herein, are meant to be non-limiting and are understood to mean "comprise," "comprises," and "comprising," respectively.

The test methods disclosed in the Test Methods Section of the present application should be used to determine the respective values of the parameters of Applicants' inventions.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated. The term "weight percent" may be denoted as "wt. %" herein.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Package

As shown in FIG. 1 the package of the present invention is to dispense a composition, wherein the package comprises:

a flexible inner container 2 made of gas-impermeable material and holding the composition wherein the composition comprises a blooming agent in an emulsified liquid form;

a sealed rigid outer container 1, which encloses the flexible inner container 2 and which is filled with a driving gas 4 compressing the inner container; and a dispenser 3 attached to the inner container 2 and in a fluid connection with the composition 5 by which the composition 5 is allowed to be dispensed by the pressure of the driving gas 4;

wherein the pressure of the driving gas 4 is higher than the vapor pressure of the emulsified liquid blooming agent in the inner container, throughout the usage of the package until the exhaustion of the composition in the inner container. See FIG. 1.

Pressures

When the driving gas is compressible such as air, Nitrogen, $CO_2$ or Nitrous Oxide ($NO_2$), the pressure of the driving gas usually reduces as the composition is dispensed from the inner container, due to the shrinkage of the inner container and the expansion of the driving gas. Alternatively, depending on the type of the driving gas, the pressure of the driving gas may be maintained at similar level throughout the usage. In any case, the pressure inside of the inner container should be the same as the pressure of the driving gas.

In any case, in the present invention, the pressure of the driving gas is always higher than the vapor pressure of emulsified liquid blooming agent, throughout the usage of the package until the exhaustion of the composition in the inner container. Preferably, the initial difference of pressure from the driving gas versus the vapor pressure of emulsified liquid blooming agent is maintained, throughout the usage of the package until the exhaustion of the composition in the inner container Thus, in the present invention, the pressure of the driving gas is higher than the vapor pressure of the emulsified liquid blooming agent throughout the usage of the package until the exhaustion of the composition in the inner container, preferably, at least about 10 psig higher, more preferably about 20 psig higher than the pressure of the vapor pressure of the emulsified liquid blooming agent.

The difference between the pressure of the driving gas and the vapor pressure of the emulsified liquid blooming agent can be up to about 40 psig preferably up to about 30 psig, more preferably up to about 25 psig.

The initial pressure of the driving gas after the inner container has been filled with the composition is preferably from about 40 to about 100 psig, more preferably from about 50 to about 90 psig, still more preferably from about 60 to about 85 psig. The preferred upper limitations are set in view of reduced safety risk in case of can failure.

The vapor pressure of the emulsified liquid blooming agent is different from the vapor pressure of non-emulsified blooming agent. However, generally speaking, when the vapor pressure of non-emulsified blooming agent is higher, the vapor pressure of the emulsified liquid blooming agent is also higher. The package of the present invention is preferably used for compositions containing a blooming agent having a higher non-emulsified vapor pressure. Such blooming agent has a non-emulsified vapor pressure of preferably from about 30 to about 80 psig, more preferably from about 40 to about 75 psig still more preferably from about 50 to about 70 psig.

Outer Rigid Container

No particular limitation is imposed on the outer rigid container used in the present invention as long as it withstands the pressure of the outer gas. For example, a metal container made of aluminum, stainless steel, steel or tin plate, a synthetic resin container made of an acetal resin or polycarbonate resin, laminated materials consisting of metals, plastics and coated papers, or a glass container may be used.

Flexible Inner Container

The flexible inner container is made of any flexible gas-impermeable material. What's meant by "flexible" herein is what can be reversibly deformed without structural damage to the inner container and/or the material. What's meant by "gas-impermeable" herein is the material substantially prevents diffusion of the gas through the material. A preferred gas-impermeable material has a gas permeability of 50 cc-mil/m$^2$-24 hr-atm or less.

Examples of such materials used for the inner container are metal, foil, plastic films, coated or modified papers, and can include a single-layer structure or laminated structure. The material should be impermeable to the propellant in the inner container and the outer gas used to maintain the pressure in the space between the inner and outer containers, provide the required toughness and chemical resistance to the various contents of the packaging. The materials used in a laminated structure can be selected to impart desired properties to the inner container either alone or in combination.

Dispenser

The dispenser may comprise any valve mechanism as long as it allows the injection of the composition into the inner container during manufacture and the dispense of the composition during consumer use.

Blooming Agent

The composition used in the present invention comprises a blooming agent. The blooming agent can be any materials that can be contained in the composition in an emulsified liquid form, and that are known in the art to foam a composition and also known as propellant.

Blooming agents are preferably a part of liquefied gas propellants category. Such blooming agent includes, for example, hydrocarbons (such as LPG—liquidized petroleum gas which is often a combination of propane, isobutane, n-Butane, Isopentane, and/or n-Pentane), hydrofluorocarbons (such as HFC134-A, HFC152-A) and unsaturated fluorocarbon (HFO-1234ze). Their common features are high purity, non-corrosive, and the pressure obtained in a container will remain essentially constant once liquefied.

For hydrocarbons, blends can be used to achieve desired intermediate vapor pressure and are essentially composed of propane, isobutane, normal Butane, isopentane and/or normal Pentane. Classifcation and nomenclature can varies depending on suppliers but as common Industry standard, the letter A or B is a reference for blend of propane, isobutane, n-butane, or blends of propane and isobutane, or blends of isobutane and n-butane. Numbers following to the letter A or B shows the average vapor pressure (non-emulsified). For example: A46 is a blend of isobutane and Propane having an average vapor pressure of 46 psig at 25° C.

The blooming agent is contained in the composition at a level of preferably from about 1% to about 15%, more preferably from about 2% to about 10%, still more preferably from about 2.5% to about 5.5% by weight of the composition. When the blooming agent such as dimethylether utilizes a vapor pressure suppressant (e.g., trichloroethane or dichloromethane), the amount of suppressant is included as part of the propellant.

The blooming agent is typically blended with the rest of the compositions using a static mixer usually for high viscous compositions or dynamic mixer usually for low viscous compositions ensuring full homogeneity before filling the inner bag.

Driving Gas

The driving gas that fills the space between the inner and the outer containers may be any gas as long as it does not penetrate the walls of the inner container. The driving gas may be the same or different than the blooming agent contained in the composition. Examples of the driving gas include, but are not limited to, air, nitrogen, carbon dioxide gas, oxygen, unsaturated fluorocarbon (HFO-1234ze), liquefied petroleum gas (LPG), dimethyl ether, and any combinations thereof. Preferably, the outer gas is an inert non-explosive gas such as nitrogen, carbon dioxide or one of the noble gases such as helium or argon. Preferably, the driving gas serves as a non-contacting propellant for dispensing the product and allows full dispensation of the product (greater than 95% of the total charging weight dispensed).

Composition

The composition used in the present invention can be any composition, including but not limited to cosmetic compositions such as hair care compositions and skin care compositions.

Preferably, the composition used in the present invention is a hair care composition, more preferably hair care composition comprising: a high melting point fatty compound; a cationic surfactant system; an aqueous carrier; and a propellant. Still more preferably, such hair care compositions have a foam density of at least about 0.3, and may also have a foam collapse resistance value of at least about 1.5 kg·m·s$^{-2}$ [N]. Such hair care compositions may also contain silicone compounds, anionic deposition polymers, soy oligomers and other additional components.

Such features and ingredients are described below in detail.

Foam Density

The composition used in the present invention preferably has a foam density of at least about 0.3, preferably at least about 0.32, more preferably at least about 0.35. The foam density is preferably to about 1.2, more preferably to about 1.1, and still more preferably to about 1.0. The foam density herein is a density of the composition as dispensed. The foam density herein is the ratio of the volumetric mass of the foam to the volumetric mass of water [1 g/mL] as the reference material.

When the foam density is too low, the composition also tends to provide reduced spreadability as the foam collapses too fast to apply desired portions of the hair, and the composition may provide reduced wet conditioning benefits such as wet detangling. When the foam density is too high, the composition may lead to uneven deposition, and thus may lead the composition to provide greasiness similar to cream product.

Preferably, the composition of the present invention has the foam density of at least about 0.3 for a period of at least about 10 seconds, more preferably at least about 20 seconds, still more preferably at least about 30 seconds, in view of providing improved wet conditioning, spreadability and/or even deposition.

Foam Collapse Resistance Value

The above composition having a specific foam density preferably has a foam collapse resistance value of at least about 1.5 kg·m·s$^{-2}$ [N], preferably at least about 1.7 kg·m·s$^{-2}$ [N], more preferably at least about 1.9 kg·m·s$^{-2}$ [N], in view of providing improved wet conditioning, spreadability and/or even deposition. Preferably, the foam collapse resistance value is to about 6.0 kg·m·s$^{-2}$ [N], more preferably to about 5.5 kg·m·s$^{-2}$ [N], still more preferably to about 5.0 kg·m·s$^{-2}$ [N].

The foam collapse resistance value is a resistance value of the foaming composition to prevent its macro structure from collapsing when putting a fixed load under compressed action on the foaming composition.

The foam collapse resistance values herein are measured by the following steps: Preparing a cylindrical vessel having an inner diameter of 29 mm and a depth of 35 mm; Preparing a load having a diameter which fits to the inner diameter of the vessel, and a thickness of minimum 5 mm to avoid any unbalanced position during compression and having a weight of maximum 2.50 g;

Filling a foaming composition in the vessel to make the vessel full and scrapping any excess before putting the load on the foaming composition;

Putting the load on the foaming composition;

Measuring resistance values while the load goes down at a speed of 10 mm per minute; and Calculate an average resistance value when the load goes down from 30% to 70% of the depth of the vessel to minimize and rule out any artifacts.

The vessel and the load can be made by any conventional materials such as plastics, preferably plastics such as thermoplastics (PLA, ABS) to avoid any additional weight added to by the compression load disk.

When the foam collapse resistance value is too low, the composition tends to provide reduced spreadability as the foam collapses too fast to apply desired portions of the hair, and the composition may provide reduced wet conditioning benefits such as wet detangling. When the foam collapse resistance value is too high, the composition tends to provide poor adhesion to hair fibers, leading to poor deposition on hair and may provide poor wet conditioning such as wet detangling.

Cationic Surfactant System

The composition used in the present invention preferably comprises a cationic surfactant system. The cationic surfactant system can be one cationic surfactant or a mixture of two or more cationic surfactants. Preferably, the cationic surfactant system is selected from: mono-long alkyl quaternized ammonium salt; a combination of mono-long alkyl quaternized ammonium salt and di-long alkyl quaternized ammonium salt; mono-long alkyl amidoamine; a combination of mono-long alkyl amidoamine and di-long alkyl quaternized ammonium salt.

The cationic surfactant system can be included in the composition at a level by weight of from about 0.1% to about 10%, preferably from about 0.5% to about 8%, more preferably from about 0.8% to about 5%, still more preferably from about 1.0% to about 4%.

Mono-Long Alkyl Quaternized Ammonium Salt

The mono-long alkyl quaternized ammonium salt cationic surfactants useful herein are those having one long alkyl chain which has from 12 to 30 carbon atoms, preferably from 16 to 24 carbon atoms, more preferably C18-22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the formula (I):

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and X$^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Preferably, one of $R^{75}$, $R^{76}$, $R^{77}$ and $R^{78}$ is selected from an alkyl group of from 12 to 30 carbon atoms, more preferably from 16 to 24 carbon atoms, still more preferably from 18 to 22 carbon atoms, even more preferably 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Nonlimiting examples of such mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt.

Mono-Long Alkyl Amidoamine

Mono-long alkyl amines are also suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al.

These amines can also be used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; more preferably l-glutamic acid, lactic acid, citric acid. The amines herein are preferably partially neutralized with any of the acids at a molar ratio of the amine to the acid of from about 1:0.3 to about 1:2, more preferably from about 1:0.4 to about 1:1. In the present invention, the amounts of these acids are not included in the amount of the cationic surfactant system, and also not included in any weight or mole ratios using the cationic surfactant system.

Di-Long Alkyl Quaternized Ammonium Salt

Di-long alkyl quaternized ammonium salt is, when used in the composition, preferably combined with a mono-long alkyl quaternized ammonium salt or mono-long alkyl amidoamine. It is believed that such combination can provide easy-to rinse feel, compared to single use of a mono-long alkyl quaternized ammonium salt or mono-long alkyl amidoamine. In such combination with a mono-long alkyl quaternized ammonium salt or mono-long alkyl amidoamine, the di-long alkyl quaternized ammonium salts are used at a level such that the wt % of the di-long alkyl quaternized ammonium salt in the cationic surfactant system is in the range of preferably from about 10% to about 50%, more preferably from about 30% to about 45%.

The di-long alkyl quaternized ammonium salt cationic surfactants useful herein are those having two long alkyl chains having 12-30 carbon atoms, preferably 16-24 carbon atoms, more preferably 18-22 carbon atoms. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Di-long alkyl quaternized ammonium salts useful herein are those having the formula (II):

wherein two of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Preferably, one of $R^{75}$, $R^{76}$, $R^{77}$ and $R^{78}$ is selected from an alkyl group of from 12 to 30 carbon atoms, more preferably from 16 to 24 carbon atoms, still more preferably from 18 to 22 carbon atoms, even more preferably 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Such di-long alkyl quaternized ammonium salt cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride. Such dialkyl quaternized ammonium salt cationic surfactants also include, for example, asymmetric dialkyl quaternized ammonium salt cationic surfactants.

High Melting Point Fatty Compound

The composition used in the present invention preferably comprises a high melting point fatty compound. The high melting point fatty compound can be included in the composition at a level of from about 0.5% to about 20%, preferably from about 1% to about 15%, more preferably from about 1.5% to about 8%, still more preferably from about 2.5% to about 7%, even more preferably from about 3.0% to about 6% by weight of the composition, in view of providing improved foam properties and improved conditioning benefits by lamellar foam structure.

The high melting point fatty compound useful herein have a melting point of 25° C. or higher, and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are preferably used in the composition of the present invention. The fatty alcohols useful herein are those having from about 14 to about 30 carbon atoms, preferably from about 16 to about 22 carbon atoms. These fatty alcohols are saturated and can be straight or branched chain alcohols. Preferred fatty alcohols include, for example, cetyl alcohol, stearyl alcohol, behenyl alcohol, and mixtures thereof.

High melting point fatty compounds of a single compound of high purity are preferred. Single compounds of pure fatty alcohols selected from the group of pure cetyl alcohol, stearyl alcohol, and behenyl alcohol are highly preferred. By "pure" herein, what is meant is that the compound has a purity of at least about 90%, preferably at least about 95%. These single compounds of high purity provide good rinsability from the hair when the consumer rinses off the composition.

Aqueous Carrier

The composition used in the present invention preferably comprises an aqueous carrier. The level and species of the carrier are selected according to the compatibility with other components, and other desired characteristic of the product.

The carrier useful in the present invention includes water and water solutions of lower alkyl alcohols and polyhydric alcohols. The lower alkyl alcohols useful herein are monohydric alcohols having 1 to 6 carbons, more preferably ethanol and isopropanol. The polyhydric alcohols useful herein include propylene glycol, hexylene glycol, glycerin, and propane diol.

Preferably, the aqueous carrier is substantially water. Deionized water is preferably used. Water from natural sources including mineral cations can also be used, depending on the desired characteristic of the product. Generally, the compositions of the present invention comprise from about 20% to about 99%, preferably from about 30% to about 95%, and more preferably from about 80% to about 95% water.

Gel Matrix

Preferably, in the composition used in the present invention, a gel matrix is formed by the cationic surfactant, the high melting point fatty compound, and an aqueous carrier. When such gel matrix is contained, the discrete particles of the oily components are dispersed in such gel matrix. The gel matrix is suitable for providing various conditioning benefits, such as slippery feel during the application to wet hair and softness and moisturized feel on dry hair.

Preferably, when the gel matrix is formed, the cationic surfactant system and the high melting point fatty compound are contained at a level such that the weight ratio of the cationic surfactant system to the high melting point fatty compound is in the range of, preferably from about 1:1 to about 1:10, more preferably from about 1:1.5 to about 1:7, still more preferably from about 1:2 to about 1:6, even more preferably from about 1:2 to about 1:4, in view of providing improved foam properties and the benefits of the present invention.

Preferably, especially when the gel matrix is formed, the total amount weight % of the cationic surfactant system and the high melting point fatty compound is from about 4.0%, more preferably from about 4.2%, still more preferably from about 4.5%, even more preferably from about 5.0%, further more preferably from about 6.0% by weight of the composition, in view of providing improved foam properties and the benefits of the present invention, and to about 15%, preferably to about 12%, more preferably to about 10%, still more preferably to about 8% by weight of the composition, in view of providing improved foam properties and the benefits of the present invention by providing desired lamellar gel network.

In the present invention, it is preferred that the cationic surfactant is included such that the mol % of the cationic surfactant to a sum of the cationic surfactant and the high melting point fatty compound is from about 18% to about 30%, more preferably from about 22% to about 28%, still more preferably from about 24% to about 27%, in view of providing improved foam properties and the benefits of the present invention. If the mol % is too low, the composition may provide more fatty alcohol crystallization and thus non-homogeneous gel matrix, leading to non-homogenous foam spreading and deposition. If the weight % is too high, the composition may provide more vesicle rather than desired lamellar sheets structure, again potentially leading to reduced wet detangling during application to hair.

Preferably, when the gel matrix is formed, the composition of the present invention is substantially free of anionic surfactants, in view of stability of the gel matrix. In the present invention, "the composition being substantially free of anionic surfactants" means that: the composition is free of anionic surfactants; or, if the composition contains anionic surfactants, the level of such anionic surfactants is very low. In the present invention, a total level of such anionic surfactants, if included, preferably 1% or less, more preferably 0.5% or less, still more preferably 0.1% or less by weight of the composition. Most preferably, the total level of such anionic surfactants is 0% by weight of the composition.

Silicone Compound

The composition used in the present invention may contain a silicone compound. The silicone compounds are included at levels by weight of the composition of from about 0.05% to about 15%, preferably from about 0.1% to about 10%, more preferably from about 0.1% to about 6%.

Preferably, the silicone compounds have an average particle size of from about 1microns to about 50 microns, in the composition.

The silicone compounds useful herein, as a single compound, as a blend or mixture of at least two silicone compounds, or as a blend or mixture of at least one silicone compound and at least one solvent, have a viscosity of preferably from about 1,000 to about 2,000,000 mPa·s at 25° C.

The viscosity can be measured by means of a glass capillary viscometer as set forth in Dow Corning Corporate Test Method CTM0004, Jul. 20, 1970. Suitable silicone fluids include polyalkyl siloxanes, polyaryl siloxanes, polyalkylaryl siloxanes, polyether siloxane copolymers, amino substituted silicones, quaternized silicones, and mixtures thereof. Other nonvolatile silicone compounds having conditioning properties can also be used.

In some embodiments, amino substituted silicones are preferably used. Preferred aminosilicones include, for example, those which conform to the general formula (I):

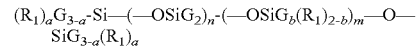

wherein G is hydrogen, phenyl, hydroxy, or $C_1$-$C_8$ alkyl, preferably methyl; a is 0 or an integer having a value from 1 to 3, preferably 1; b is 0, 1 or 2, preferably 1; n is a number from 0 to 1,999; m is an integer from 0 to 1,999; the sum of n and m is a number from 1 to 2,000; a and m are not both 0; $R_1$ is a monovalent radical conforming to the general formula $CqH_{2q}L$, wherein q is an integer having a value from 2 to 8 and L is selected from the following groups: —$N(R_2)CH_2$—$CH_2$—$N(R_2)_2$; —$N(R_2)_2$; —$N(R_2)_3A^-$; —$N(R_2)CH_2$—$CH_2$—$NR_2H_2A^-$; wherein $R_2$ is hydrogen, phenyl, benzyl, or a saturated hydrocarbon radical, preferably an alkyl radical from about $C_1$ to about $C_{20}$; $A^-$ is a halide ion.

Highly preferred amino silicones are those corresponding to formula (I) wherein m=0, a=1, q=3, G=methyl, n is preferably from about 1500 to about 1700, more preferably about 1600; and L is —$N(CH_3)_2$ or —$NH_2$, more preferably —$NH_2$. Another highly preferred amino silicones are those corresponding to formula (I) wherein m=0, a=1, q=3, G=methyl, n is preferably from about 400 to about 600, more preferably about 500; and L is —$N(CH_3)_2$ or —$NH_2$, more preferably —$NH_2$. Such highly preferred amino silicones can be called as terminal aminosilicones, as one or both ends of the silicone chain are terminated by nitrogen containing group.

The above aminosilicones, when incorporated into the composition, can be mixed with solvent having a lower viscosity. Such solvents include, for example, polar or non-polar, volatile or non-volatile oils. Such oils include, for example, silicone oils, hydrocarbons, and esters. Among such a variety of solvents, preferred are those selected from the group consisting of non-polar, volatile hydrocarbons, volatile cyclic silicones, non-volatile linear silicones, and mixtures thereof. The non-volatile linear silicones useful herein are those having a viscosity of from about 1 to about 20,000 centistokes, preferably from about 20 to about 10,000 centistokes at 25° C. Among the preferred solvents, highly preferred are non-polar, volatile hydrocarbons, especially non-polar, volatile isoparaffins, in view of reducing the viscosity of the aminosilicones and providing improved hair conditioning benefits such as reduced friction on dry hair. Such mixtures have a viscosity of preferably from about 1,000 mPa·s to about 100,000 mPa·s, more preferably from about 5,000 mPa·s to about 50,000 mPa·s.

Other suitable alkylamino substituted silicone compounds include those having alkylamino substitutions as pendant groups of a silicone backbone. Highly preferred are those known as "amodimethicone". Commercially available amodimethicones useful herein include, for example, BY16-872 available from Dow Corning.

Anionic Deposition Polymer

The composition used in the present invention may further comprise an anionic polymer, preferably anionic deposition polymer, in view of improving out of shower styling and manageability of hair to achieve the desired style. The deposition polymer is included at a level by weight of the composition of, from about 0.05% to about 6%, preferably from about 0.1% to about 5%, more preferably from about 0.2% to about 3.5%.

The anionic polymers useful herein are those comprising a vinyl monomer (A) with a carboxyl group, wherein the vinyl monomer (A) is contained in the polymer at a level of from about 10 mass % to 90 mass % based on the total mass of the copolymer.

Especially for anionic deposition polymers, it is preferred that the weight ratio of (i) the anionic deposition polymer to (ii) a sum of the cationic surfactant and high melting point fatty compound is from about 1:1 to about 1:160, more preferably from about 1:2.5 to about 1:120, still more preferably from about 1:3.5 to about 1:80. If the weight ratio of (i) to (ii) is too low, the composition may provide lower deposition of cationic surfactants, high melting point fatty compounds, and/or silicone compounds. If the weight ratio of (i) to (ii) is too high, the composition may influence rheology, and may undesirably decrease rheology of the composition.

Anionic Deposition Polymer

The deposition polymer useful herein is a copolymer comprising: a vinyl monomer (A) with a carboxyl group in the structure; and a vinyl monomer (B) expressed by the following formula (1):

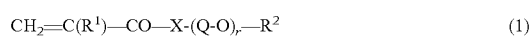

wherein: $R^1$ represents a hydrogen atom or a methyl group; $R^2$ represents a hydrogen atom or an alkyl group with from 1 to 5 carbon atoms, which may have a substitution group; Q represents an alkylene group with from 2 to 4 carbon atoms which may also have a substitution group; r represents an integer from 2 to 15; and X represents an oxygen atom or an NH group; and, in the following structure -(Q-O)$_r$—$R^2$, the number of atoms bonded in a straight chain is 70 or less; and wherein the vinyl monomer (A) is contained at a level of from about 10 mass % to about 90 mass %, and the vinyl monomer (B) is contained at level of from about 10 mass % to about 90 mass %.

Vinyl Monomer (A)

The copolymer of the present invention contains a vinyl monomer (A) having a carboxyl group in the structure. The copolymer may contain one type of the vinyl monomer (A), or may contain two or more types of the vinyl monomer (A). The vinyl monomer (A) is preferably anionic.

Non-limited example of the vinyl monomer (A) having a carboxyl group include, for example, unsaturated carboxylic acid monomers having 3 to 22 carbon atoms. The unsaturated carboxylic acid monomer has, preferably 4 or more carbon atoms, and preferably 20 or less carbon atoms, more preferably 18 or less carbon atoms, still more preferably 10 or less carbon atoms, and even more preferably 6 or less carbon atoms. Furthermore, the number of carboxyl groups in the vinyl monomer (A) is preferably from 1 to 4, more preferably from 1 to 3, even more preferably from 1 to 2, and most preferably 1.

In view of improved deposition of cationic surfactants, fatty compounds and/or silicones, the vinyl monomer (A) is preferably an unsaturated carboxylic acid monomer expressed by the following formula (2) or formula (3), more preferably those expressed by the formula (2)

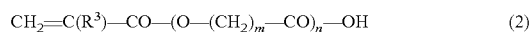

wherein: $R^3$ represents a hydrogen atom or a methyl group, preferably a hydrogen atom; m represents an integer of 1 through 4, preferably 2 to 3; and n represents an integer of 0 through 4, preferably 0 to 2, and most preferably 0

wherein: $R^4$ represents a hydrogen atom or a methyl group, preferably a hydrogen atom; p and q independently represent an integer of 2 through 6, preferably 2 to 3.

Examples of those expressed by the formula (2) include (meth)acrylic acid, crotonic acid, maleic acid, fumaric acid, itaconic acid, angelic acid, tiglic acid, 2-carboxy ethyl acrylate oligomer, and the like. Among them, preferred are acrylic acid and methacrylic acid, and more preferred is acrylic acid. Examples of those expressed by the formula (3) include acryloyloxy ethyl succinate, 2-methacryloyloxy ethyl succinate, and the like.

Vinyl Monomer (B)

The copolymer contains a vinyl monomer (B). The copolymer may contain one type of the vinyl monomer (B), or may contain two or more types of the vinyl monomer (B). The vinyl monomer (B) is preferably nonionic.

The Vinyl monomers (B) useful herein are those expressed by formula (4)

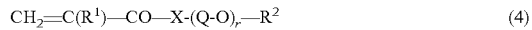

$$CH_2=C(R^1)-CO-X-(Q-O)_r-R^2 \quad (4)$$

wherein: $R^1$ represents a hydrogen atom or a methyl group; $R^2$ represents a hydrogen atom or an alkyl group with 1 through 5 carbon atoms, which may have a substitution group; Q represents an alkylene group with 2 through 4 carbon atoms which may also have a substitution group; r represents an integer from 2 through 15; and X represents an oxygen atom or an NH group; and in the structure $-(Q-O)_r-R^2$, the number of atoms bonded in a straight chain is 70 or less.

If $R^2$ has a substitution group, the substitution group is a substitution group that does not react with other parts of the copolymer. The vinyl monomer (B) is preferably hydrophilic, and therefore $R^2$ is preferably a hydrogen atom or an alkyl group with 1~3 carbon atoms, and more preferably a hydrogen atom or an alkyl group with 1 or 2 carbon atoms.

X preferably represents an oxygen atom.

Q represents preferably an alkylene group with 2 through 3 carbon atoms which may also have a substitution group, and more preferably an alkylene group with 2 through 3 carbon atoms without any substitution group. If the alkylene group of Q has a substitution group, it is preferred that such substitution group does not react with other parts of the copolymer, more preferably such substitution group has a molecular weight of 50 or less, still more preferably such substitution group has a molecular weight that is smaller than the structural moiety of $-(Q-O)r-$. Examples of such substitution group include a hydroxyl group, methoxy group, ethoxy group, and the like.

r represents preferably 3 or higher, and preferably 12 or less, in view of improved deposition of cationic surfactants, fatty compounds and/or silicones, and/or in view of smoothness during application.

As described above, in the structure $-(Q-O)r-R^2$, the number of atoms that are bonded by the straight chain is 70 or less. For example, if Q represents an n-butylene group, r=15, and $R^2$ represents an n-pentyl group, the number of atoms that are bonded in the straight chain of the structure $-(Q-O)r-R^2$ is calculated as 80, which therefore is outside of the scope. The number of atoms bonded in the straight chain in the structure $-(Q-O)r-R^2$ is preferably 60 or less, more preferably 40 or less, even more preferably 28 or less, and particularly preferably 20 or less, in view of improved deposition of cationic surfactants, fatty compounds and/or silicones, and/or in view of smoothness during application.

Examples of the vinyl monomer (B) include, methoxy polyethylene glycol (meth)acrylate (where the number of repetitions of polyethylene glycol (r in formula (4)) is between 2~15), polyethylene glycol (meth)acrylate (where the number of repetitions of polyethylene glycol (r in formula (4)) is between 2~15), methoxy polyethylene glycol/polypropylene glycol (meth)acrylate (where the number of repetitions of polyethylene glycol/polypropylene glycol (r in formula (4)) is between 2~15), polyethylene glycol/polypropylene glycol (meth)acrylate (where the number of repetitions of polyethylene glycol/polypropylene glycol (r in formula (4)) is between 2~15), methoxy polyethylene glycol/polybutylene glycol (meth)acrylate (where the number of repetitions of polyethylene glycol/polybutylene glycol (r in formula (4)) is between 2~15), polyethylene glycol/polybutylene glycol (meth)acrylate (where the number of repetitions of polyethylene glycol/polybutylene glycol (r in formula (4)) is between 2~15), methoxy polyethylene glycol (meth)acrylamide (where the number of repetitions of polyethylene glycol (r in formula (4)) is between 2~15), and polyethylene glycol (meth)acrylamide (where the number of repetitions of polyethylene glycol (r in formula (4)) is between 2~15); preferably methoxy polyethylene glycol (meth)acrylate (where the number of repetitions of polyethylene glycol (r in formula (4)) is between 3~12), polyethylene glycol (meth)acrylate (where the number of repetitions of polyethylene glycol (r in formula (4)) is between 3~12), methoxy polyethylene glycol/polypropylene glycol (meth)acrylate (where the number of repetitions of polyethylene glycol/polypropylene glycol (r in formula (4)) is between 3~12), polyethylene glycol/polypropylene glycol (meth)acrylate (where the number of repetitions of polyethylene glycol/polypropylene glycol (r in formula (4)) is between 3~12), methoxy polyethylene glycol/polybutylene glycol (meth)acrylate (where the number of repetitions of polyethylene glycol/polybutylene glycol (r in formula (4)) is between 3~12), polyethylene glycol/polybutylene glycol (meth)acrylate (where the number of repetitions of polyethylene glycol/polybutylene glycol (r in formula (4)) is between 3~12); more preferably methoxy polyethylene glycol (meth)acrylate (where the number of repetitions of polyethylene glycol (r in formula (4)) is between 3~12), and polyethylene glycol (meth)acrylate (where the number of repetitions of polyethylene glycol (r in formula (4)) is between 3~12).

Vinyl Monomer (C)

In addition to the vinyl monomers (A) and (B), the copolymer may further contain a vinyl monomer (C) having an alkyl group with 12~22 carbon atoms, in view of providing conditioning effect such as smoothness during application. When included, the amount of the vinyl monomer (C) is preferably 40 mass % or less, more preferably 30 mass % or less, even more preferably 25 mass % or less, and still more preferably 20 mass % or less based on the total mass of the copolymer, in view of improved deposition of cationic surfactants, fatty compounds and/or silicones, and/or in view of smoothness during application.

Preferably, the vinyl monomer (C) is a (meth)acrylate monomer having an alkyl group with 12~22 carbon atoms, in view of smoothness during application. Furthermore, vinyl monomers with branched alkyl groups are particularly preferred.

Examples of the (meth)acrylate monomer having an alkyl group with 12~22 carbon atoms include myristyl (meth)acrylate, isostearyl (meth)acrylate, stearyl (meth)acrylate, behenyl (meth)acrylate, cetyl (meth)acrylate, lauryl (meth)acrylate, synthetic lauryl (meth)acrylate, (however "synthetic lauryl (meth)acrylate" refers to an alkyl (meth)acrylate having alkyl groups with 12 carbon atoms and alkyl groups with 13 carbon atoms), and the like. Of these, (meth)acrylate monomers having an alkyl group with 12~20 carbon atoms are preferable, and (meth)acrylate monomers having an alkyl group with 16~18 carbon atoms are more preferable.

The copolymer may contain one type of the vinyl monomer (C), or may contain two or more types of the vinyl monomer (C).

Other Monomers

In addition to the aforementioned vinyl monomers (A), (B), and (C), the copolymer may also contain other vinyl monomers, to the extent not to deteriorate the effect of the copolymer. Examples of other vinyl monomers include nonionic monomers, amphoteric monomers, semipolar monomers, cationic monomers, as well as monomers containing a polysiloxane group, preferably nonionic monomers with or without polysiloxane group These other monomers are different from any of the aforementioned vinyl monomers (A), (B), and (C).

Normally the amount of such other monomers, if included, is 40 mass % or less of the total mass of the copolymer, preferably 30 mass % or less, more preferably 20 mass % or less, and even more preferably 10 mass % or less.

In view of improved deposition of cationic surfactants, fatty compounds, and/or silicones, the amount of cationic functional groups in the copolymer is preferably low, and for example cationic functional groups preferably account for 10 mole % or less of all functional groups in the copolymer. More preferably, the copolymer is free of cationic functional groups.

Examples of nonionic monomers include esters of (meth)acrylic acid and alcohols with 1~22 carbon atoms, amides of (meth)acrylic acid and alkyl amines with 1~22 carbon atoms, monoesters of (meth)acrylic acid and ethylene glycol, 1,3-propylene glycol or the like, as well as esters where the hydroxyl group of the monoester has been etherified by methanol, ethanol or the like, (meth)acryloyl morpholine and the like.

Examples of amphoteric monomers include (meth)acryl esters having a betaine group, (meth)acrylamide having a betaine group and the like.

Examples of semipolar monomers include (meth)acrylate esters having an amine oxide group, (meth)acrylamides having an amine oxide group, and the like.

Examples of cationic monomers include (meth)acrylate esters having a quaternary ammonium group, (meth)acrylamides having a quaternary ammonium group and the like.

The monomer containing a polysiloxane group is a monomer having a polysiloxane structure and also having a structure that can bond by covalent bond to the copolymer. These component units have high affinity towards silicone oil that is normally used in conjunction in cosmetic material compositions, and are thought to act by bonding the silicone oil to the other component units in the copolymer and thus increasing the adsorption force of silicone oil to the skin and hair, particularly damaged hair.

The polysiloxane structure is a structure where two or more repeating structural units expressed by the following formula (4) are linked.

$$—(SiR^5R^6—O)— \qquad (4)$$

In formula (4), $R^5$ and $R^6$ independently represent an alkyl group with 1 to 3 carbon atoms or a phenyl group.

The structure that can link via covalent bond to the copolymer can be a structure that has a vinyl structure such as a (meth)acrylate ester, or (meth)acrylamide and that can copolymerize with another monomer, a structure that has a functional group such as a thiol, that can link to the copolymer by chain transfer during polymerization, or a structure that has an isocyanate group, carboxylic acid group, hydroxyl group, amino group, or the like, and that can react and link to the functional groups on the copolymer, but there is no restriction to these structures.

A plurality of these linkable structures can be present in one monomer containing a polysiloxane group. In the copolymer, the polysiloxane structure can link by a graft structure to the main chain, or conversely the polysiloxane structure can be the main chain with the other structure link by a graft structure, and in addition the polysiloxane structure and the other structure can be linked in a straight chain condition by a block structure.

The monomer containing a polysiloxane group is preferably expressed by the following formula (5).

$$CH_2=C(R^7)—Z—(SiR^8R^9—O)_s—R^{10} \qquad (5)$$

In the formula, $R^7$ represents a hydrogen atom or a methyl group, $R^8$ and $R^9$ independently represent an alkyl group with 1 to 3 carbon atoms or a phenyl group, $R^{19}$ represents an alkyl group with 1 to 8 carbon atoms, Z represents a bivalent linking group or a direct bond, and s represents an integer between 2 to 200.

More preferably, s is 3 or higher, and even more preferably, s is 5 or higher, in view of increased affinity to silicone oil, and preferably s is 50 or less, in view of enhanced copolymerization with the other monomers.

Z represents a bivalent linking group or a direct bond, but a linking group containing one or a combination of two or more of the structures suggested below is preferable. The numbers that are combined is not particularly restricted, but normally is 5 or less. Furthermore, the direction of the following structures are arbitrary (the polysiloxane group side can be on either end). Note, in the following, R represents an alkylene group with 1 to 6 carbon atoms or a phenylene group.

—COO—R—
—CONH—R—
—O—R—
—R—

The monomer expressed by the aforementioned formula (5), include, for example, α-(vinyl phenyl) polydimethyl siloxane, α-(vinyl benzyloxy propyl) polydimethyl siloxane, α-(vinyl benzyl) polymethyl phenyl siloxane, α-(methacryloyl oxypropyl) polydimethyl siloxane, α-(methacryloyloxy propyl) polymethyl phenyl siloxane, α-(methacryloyl amino propyl) polydimethyl siloxane and the like. The monomer containing a polysiloxane group can be a single type, or can be two or more types used in combination.

In order to adjust the molecular weight and the viscosity of the copolymer, a cross-linking agent such as a polyfunctional acrylate or the like can be introduced to the copolymer. However, in this invention, it is preferred that a cross-linking agent is not included in the copolymer.

Structure Analysis

The amount of the vinyl monomers (A), (B), and (C) as well as other monomers in the copolymer can be measured using IR absorption or Raman scattering by the carbonyl groups, amide bonds, polysiloxane structures, various types of functional groups, carbon backbone and the like, by $^1$H-NMR of methyl groups in the polydimethyl siloxane, amide bond sites, and methyl groups and methylene groups adjacent thereto, as well as various types of NMR represented by $^{13}$C-NMR and the like.

Weighted Average Molecular Weight

The weighted average molecular weight of the copolymer is preferably about 3,000 or higher, more preferably about 5,000 or higher, and even more preferably about 10,000 or higher, in view of providing conditioning effect via foaming a complex with cationic surfactant, and preferably to about 2,000,000, more preferably about 1,000,000 or less, still more preferably about 500,000 or less, even more preferably about 100,000 or less, and most preferably about 50,000 or less, in view of feeling after drying.

The weighted average molecular weight of the copolymer can be measured by gel permeation chromatography (GPC). The development solvent that is used in gel permeation chromatography is not particularly restricted so long as being a normally used solvent, but for example, the measurement can be performed using a solvent blend of water/methanol/acetic acid/sodium acetate.

Viscosity

The copolymer preferably has a viscosity for a 20 mass % ethanol solution at 25° C. of 5 mPa·s or higher and 20,000 mPa·s or less. The viscosity is more preferably 10 mPa·s or higher, even more preferably 15 mPa·s or higher, but on the other hand is more preferably 10,000 mPa·s or less, and even more preferably 5,000 mPa·s or less. The viscosity of the copolymer is preferably 5 mPa·s or higher and 20,000 mPa·s or less, from the perspective of handling. The viscosity can be measured using a B-type viscometer.

Similar to the weighted average molecular weight, the viscosity of the copolymer can be adjusted by controlling the degree of polymerization of the copolymer, and can be controlled by increasing or decreasing the amount of a cross-linking agent such as a polyfunctional acrylate or the like that is added.

Soy Oligomer

The composition used in the present invention may further comprise a mixture of a soy oligomer and soy bean oil, in view of improving out of shower styling and manageability of hair to achieve the desired style.

The hair care composition comprises such soy oligomer at a level of from about 0.005% to about 5%, preferably from about 0.01% to about 3%, more preferably from about 0.01% to about 2%, still more preferably from about 0.01% to about 1% by weight of the hair care composition. The hair care composition comprises such soy bean oil at a level of from about 0.005% to about 20%, preferably from about 0.01% to about 15%, more preferably from about 0.03% to about 10%, still more preferably from about 0.03% to about 5%, by weight of the hair care composition. The weight ratio of the soy bean oil to the soy oligomer is preferably from about 98:2 to about 70:30, more preferably from about 95:5 to about 75:25, still more preferably from about 95:5 to about 80:20.

Oligomers useful herein include, for example, dimer, trimer, tetramer, pentamer, and/or hexamer, preferably, dimer, trimer, and/or tetramer, more preferably, a mixture of dimer, trimer, and/or tetramer. The oligomers may be further modified via hydrogenation. For example, in certain embodiments, the oligomer can be about 60% hydrogenated or more; in certain embodiments, about 70% hydrogenated or more; in certain embodiments, about 80% hydrogenated or more; in certain embodiments, about 85% hydrogenated or more; in certain embodiments, about 90% hydrogenated or more; and in certain embodiments, generally 100% hydrogenated.

Additional Components

The composition used in the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

A wide variety of other additional components can be formulated into the present compositions.

These include, for example, conditioning agents such as hydrolysed collagen with tradename Peptein 2000 available from Hormel, vitamin E with tradename Emix-d available from Eisai, panthenol available from Roche, panthenyl ethyl ether available from Roche, hydrolysed keratin, proteins, plant extracts, and nutrients; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; coloring agents, such as any of the FD&C or D&C dyes; perfumes; ultraviolet and infrared screening and absorbing agents such as benzophenones; and antidandruff agents such as zinc pyrithione.

Product Forms

The composition used in the present invention can be in the form of rinse-off products or leave-on products, preferably rinse-off products. The composition used in the present invention is preferably a hair care composition which can be used as a wide variety of hair care products, including but not limited to hair conditioning products, hair treatment products, and hair styling products.

The composition used in the present invention is especially preferably a rinse-off hair conditioner. Such compositions are preferably used by following steps:
(i) after shampooing hair, applying to the hair an effective amount of the conditioning compositions for conditioning the hair; and
(ii) then rinsing the hair.

Key Features of the Inventions a. The present invention is directed to a package to dispense a composition, wherein the package comprises:
   a flexible inner container made of gas-impermeable material and holding the composition wherein the composition comprises a blooming agent in an emulsified liquid form;
   a sealed rigid outer container which encloses the flexible inner container and which is filled with a driving gas compressing the inner container; and
   a dispenser attached to the inner container and in a fluid connection with the composition by which the composition is allowed to be dispensed by the pressure of the driving gas;
   wherein the pressure of the driving gas is higher than the vapor pressure of the emulsified liquid blooming agent in the inner container, throughout the usage of the package until the exhaustion of the composition in the inner container.

b. The package of the above feature, wherein the initial pressure of the driving gas after the inner container has been filled with the composition is preferably from about 40 to about 100 psig, more preferably from about 50 to about 90 psig, still more preferably from about 60 to about 85 psig.

c. The package of the any of the preceding features, wherein the blooming agent has a non-emulsified vapor pressure of preferably from about 30 to about 80 psig, more preferably from about 40 to about 75 psig, still more preferably from about 50 to about 70 psig.

d. The package of the any of the preceding features, wherein the composition has a foam density of preferably at least about 0.3.

e. The package of the any of the preceding features, wherein the composition has the foam density of at least about 0.3, preferably for at least about 10 seconds, more preferably for at least about 20 seconds, still more preferably for at least about 30 seconds.

f. The package of any of the preceding features, wherein the composition is dispensed as a delayed foam and/or gradual foam, and wherein it takes for at least about 10 seconds, preferably at least about 20 seconds, more preferably at least about 30 seconds for the composition to be completely foamed.
g. The package of any of the preceding features, wherein the composition comprises by weight of the composition, from about 2% to about 10% of the blooming agent, preferably from about 2.5% to about 5.5% of the blooming agent
h. The package of any of the preceding features, wherein the composition is a hair care composition further comprising:
   a high melting point fatty compound;
   a cationic surfactant system; and
   an aqueous carrier.
i. The package of any of the preceding features, wherein the composition comprises by weight of the composition, from about 1.5% to about 8% of the one or more high melting point fatty compounds, preferably from about 2.5% to about 7%, more preferably from about 3.0% to about 6% of the one or more high melting point fatty compounds.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

TABLE 1

| | Components | Ex. 1 | CEx. i | CEx. ii | Ex. 2 | CEx. iii |
|---|---|---|---|---|---|---|
| Compositions (wt %) | Stearamidopropyl dimethyl amine | 1.94 | 1.94 | 1.94 | 1.94 | 1.94 |
| | L-glutamic acid | 0.63 | 0.63 | 0.63 | 0.63 | 0.63 |
| | Behenyl trimethylammonium methosulfate | — | — | — | — | — |
| | Dicetyldimonium chloride | — | — | — | — | — |
| | Cetyl alcohol | 1.68 | 1.68 | 1.68 | 1.68 | 1.68 |
| | Stearyl alcohol | 2.90 | 2.90 | 2.90 | 2.90 | 2.90 |
| | Glycerin | — | — | — | — | — |
| | Silicone | 0.5 | 0.5 | 0.5 | 0.5 | 0.5 |
| | Anionic deposition polymer | — | — | — | — | — |
| | Soy oligomer and soybean oil | — | — | — | — | — |
| | Preservatives | 0.5 | 0.5 | 0.5 | 0.5 | 0.5 |
| | Perfume | 0.5 | 0.5 | 0.5 | 0.5 | 0.5 |
| | Deionized Water | 82.31 | 82.31 | 82.31 | 82.31 | 82.31 |
| | Blooming agent | 3 | 3 | 3 | 3 | 3 |
| | Type of Blooming agent (Vapor pressure of non-emulsified blooming agent (psig, @ 25° C.)) | B75 (70-76) | B75 (70-76) | A31 (28-34) | A31 (28-34) | HFO (46-48) |
| Packaging specification | | Comprising a flexible inner container made of gas-impermeable material and holding the composition; a sealed rigid outer container which encloses the flexible inner container and which is filled with a driving gas compressing the inner container; and a dispenser attached to the inner container and in a fluid connection with the composition by which the composition is allowed to be dispensed by the pressure of the driving gas Rigid outer container (Can) volume (brimful): 350 ml. Flexible inner container (Bag-on-valve) filled volume/empty: 215/15 ml. Valve: 2 orifices .035" × .090". Actuator: not restrictive of flow rate. Driving gas pressures account also for the air inside the can before filling (no vacuum filling). | | | | |
| Driving gas | Pressure of Driving gas (psig) [initial, final] | [80, 40] | [60, 15] | [50, 15] | [50, 50] | [50, 50] |
| | Type of Driving gas | Compressed air | Compressed air | HFO-1234ze 3 g | HFO-1234ze 7 g | HFO-1234ze 7 g |
| Properties and Benefits | Foam density as dispensed | 0.4 | 0.7 | 0.7 | 0.6 | 0.6 |
| | Sputtering/noise throughout the exhaustion of the can is observed? | Minimum noise/no sputtering | Yes | Yes | Minimum noise/no sputtering | Yes |
| | Residue | <5 wt % | >30 wt % | >15 wt % | <5 wt % | >15 wt % |

TABLE 2

| Components | | Ex. 3 | CEx. iv | CEx. v | Ex. 4 |
|---|---|---|---|---|---|
| Compositions (wt %) | Stearamidopropyl dimethyl amine | — | — | — | — |
| | L-glutamic acid | — | — | — | — |
| | Behenyl trimethylammonium methosulfate | 2.85 | 2.85 | 2.85 | 2.85 |
| | Dicetyldimonium chloride | — | — | — | — |
| | Cetyl alcohol | 1.0 | 1.0 | 1.0 | 1.0 |
| | Stearyl alcohol | 2.52 | 2.52 | 2.52 | 2.52 |
| | Glycerin | — | — | — | — |
| | Silicone | — | — | — | — |
| | Anionic deposition polymer | 0.5 | 0.5 | 0.5 | 0.5 |
| | Soy oligomer and soybean oil | — | — | — | — |
| | Preservatives | 0.5 | 0.5 | 0.5 | 0.5 |
| | Perfume | 0.5 | 0.5 | 0.5 | 0.5 |
| | Deionized Water | 88.13 | 88.13 | 86.13 | 86.13 |
| | Blooming agent | 3 | 3 | 5 | 5 |
| | Type of Blooming agent (Vapor pressure of non-emulsified blooming agent (psig, @ 25° C.)) | B75 (70-76) | B75 (70-76) | B45 (43-48) | B30 (27-33) |
| Packaging specification | | Comprising a flexible inner container made of gas-impermeable material and holding the composition; a sealed rigid outer container which encloses the flexible inner container and which is filled with a driving gas compressing the inner container; and a dispenser attached to the inner container and in a fluid connection with the composition by which the composition is allowed to be dispensed by the pressure of the driving gas Rigid outer container (Can) volume (brimful): 350 ml. Flexible inner container (Bag-on-valve) filled volume/empty: 215/15 ml. Valve: 2 orifices .035" × .090". Actuator: not restrictive of flow rate. Driving gas pressures account also for the air inside the can before filling (no vacuum filling). | | | |
| Driving gas | Pressure of Driving gas (psig) [initial, final] | [80, 40] | [60, 15] | [60, 15] | [60, 15] |
| | Type of Driving gas | Compressed air | Compressed air | Compressed air | Compressed air |
| Properties and Benefits | Foam density as dispensed | 0.6 | 0.8 | 0.8 | 0.9 |
| | Sputtering/noise throughout the exhaustion of the can is observed? | Minimum noise/no sputtering | Yes | Yes | Minimum noise/no sputtering |
| | Residue | <5 wt % | >30 wt % | >30 wt % | <10 wt % |

Method of Preparation

The packages of "Ex. 1" through "Ex. 4" of the present invention and packages of "CEx. i" through "CEx. v" as comparative examples can be prepared by any conventional method well known in the art. In all examples, the blooming agents were in emulsified liquid form, at least at the time of initial usage.

Properties and Benefits

Examples 1 through 4 are packages of the present invention, containing hair care compositions which are particularly useful as rinse-off hair conditioning compositions. After shampooing hair, an effective amount of the hair care compositions are applied to the hair, and then rinsed off.

In the packages of "Ex. 1" through "Ex. 4" of the present invention, the pressure of the driving gas is higher than the vapor pressure of the emulsified liquid blooming agent in the inner container, throughout the usage of the package until the exhaustion of the composition in the inner container. On the other hand, in the packages of "CEx. i" through "CEx. v" as comparative examples, the pressure of the driving gas becomes lower or equal to the vapor pressure of emulsified liquid blooming agent, at some point of the usage.

The embodiments disclosed and represented by the previous "Ex. 1" through "Ex. 4" have many advantages. For example, they provide reduced sputtering, reduced noise when dispensing, and/or reduced an amount of residues which are compositions remaining in the package. Such advantages can also be seen by the comparison between these embodiments and the comparative examples.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A package and a composition comprising:
   a flexible inner container made of gas-impermeable material and holding the composition wherein the composition comprises:
   from about 0.5% to about 8% of a cationic surfactant;
   from about 2.5% to about 7% high melting point fatty compound wherein the high melting point fatty compound is selected from the group consisting of cetyl alcohol, stearyl alcohol, behenyl alcohol, and mixtures thereof;
   from about 0.05% to about 15% of a silicone compound wherein the silicone compounds have an average particle size of from about 1 micron to about 50 microns;
   from about 2% to about 10% of a blooming agent in an emulsified liquid form wherein the blooming agent is selected from the group consisting of propane, isobutane, blends of propane and isobutane, HFO, and combinations thereof;
   a sealed rigid outer container which encloses the flexible inner container and which is filled with a driving gas compressing the inner container; and
   a dispenser attached to the inner container and in a fluid connection with the composition by which the composition is allowed to be dispensed by the pressure of the driving gas; wherein the pressure of the driving gas is higher than the vapor pressure of the emulsified liquid blooming agent in the inner container, throughout the usage of the package until the exhaustion of the composition in the inner container.

2. The package and composition of claim 1, wherein the initial pressure of the driving gas after the inner container has been filled with the composition is from about 40 to about 100 psig.

3. The package and composition of claim 1, wherein the initial pressure of the driving gas after the inner container has been filled with the composition is from about 50 to about 90 psig.

4. The package and composition of claim 1, wherein the initial pressure of the driving gas after the inner container has been filled with the composition is from about 60 to about 85 psig.

5. The package and composition of claim 1, wherein the blooming agent has a non-emulsified vapor pressure of from about 30 to about 80 psig.

6. The package and composition of claim 1, wherein the blooming agent has a non-emulsified vapor pressure of from about 40 to about 75 psig.

7. The package and composition of claim 1, wherein the blooming agent has a non-emulsified vapor pressure of from about 50 to about 70 psig.

8. The package and composition of claim 1, wherein the composition has a foam density of at least about 0.3.

9. The package and composition of claim 1, wherein the composition has the foam density of at least about 0.3 for at least about 10 seconds.

10. The package and composition of claim 1, wherein the composition has the foam density of at least about 0.3 for at least about 20 seconds.

11. The package and composition of claim 1, wherein the composition has the foam density of at least about 0.3 for at least about 30 seconds.

12. The package and composition of claim 1, wherein the composition is dispensed as a delayed foam and/or gradual foam, and wherein it takes for at least about 10 seconds for the composition to be completely foamed.

13. The package and composition of claim 12, wherein it takes for at least about 20 seconds for the composition to be completely foamed.

14. The package and composition of claim 13, wherein it takes for at least about 30 seconds for the composition to be completely foamed.

15. The package and composition of claim 1, wherein the composition comprises by weight of the composition, from about 2% to about 10% of the blooming agent.

16. The package and composition of claim 1, wherein the composition comprises by weight of the composition, from about 2.5% to about 5.5% of the blooming agent.

17. The package and composition of claim 1, wherein the composition comprises by weight of the composition, from about 3.0% to about 6% of the one or more high melting point fatty compounds.

* * * * *